United States Patent [19]

Green et al.

[11] Patent Number: 5,330,489
[45] Date of Patent: Jul. 19, 1994

[54] STERNUM CLOSURE BUCKLE

[75] Inventors: David T. Green, Westport; Henry Bolanos, East Norwalk; Thomas W. Alesi, Jr., New Fairfield, all of Conn.

[73] Assignee: United States Surgical Corporation, Norwalk, Conn.

[21] Appl. No.: 959,164

[22] Filed: Oct. 9, 1992

[51] Int. Cl.⁵ .................................................. A61B 17/08
[52] U.S. Cl. .................................... 606/151; 606/213; 24/170
[58] Field of Search ............... 606/151, 157, 191, 213, 606/215, 216, 218; 24/191, 193, 16 PB, 170

[56] References Cited

U.S. PATENT DOCUMENTS

| | | |
|---|---|---|
| 1,717,766 | 6/1929 | Eimler . |
| 1,950,799 | 3/1934 | Jones . |
| 2,194,953 | 3/1940 | Painter ................................ 24/191 |
| 2,622,292 | 12/1952 | Pehaczek . |
| 2,948,939 | 8/1960 | Prete, Jr. . |
| 2,987,062 | 6/1961 | Ellison . |
| 3,111,945 | 11/1963 | Von Solbrig .. |
| 3,469,573 | 9/1969 | Florio . |
| 3,535,764 | 8/1985 | Ebert . |
| 3,570,497 | 3/1971 | Lemole . |
| 3,577,601 | 5/1971 | Mariani . |
| 3,802,438 | 4/1974 | Wolvek . |
| 4,037,603 | 7/1977 | Wendorff . |
| 4,119,091 | 10/1978 | Partridge . |
| 4,201,215 | 5/1980 | Crossett et al. . |
| 4,263,904 | 4/1981 | Judet . |
| 4,279,248 | 7/1981 | Gabbay . |
| 4,373,528 | 10/1969 | Mishkin et al. . |
| 4,387,489 | 6/1983 | Dudek . |
| 4,428,376 | 1/1984 | Mericle ............................. 606/154 |
| 4,512,346 | 4/1985 | Lemole . |
| 4,583,541 | 4/1986 | Barry . |
| 4,625,717 | 12/1986 | Covitz . |
| 4,643,178 | 2/1987 | Nastari et al. . |
| 4,667,662 | 5/1987 | Titone et al. . |
| 4,730,615 | 3/1988 | Sutherland et al. ............. 128/335 |
| 4,754,530 | 7/1988 | Lindblad .......................... 24/169 |
| 4,792,336 | 12/1988 | Hlavacek et al. ............... 623/13 |
| 4,802,477 | 2/1989 | Gabbay ............................ 128/137 |
| 4,804,383 | 2/1989 | Rey et al. ......................... 623/13 |
| 4,813,416 | 3/1989 | Pollak et al. .................... 128/335 |
| 4,878,271 | 11/1989 | Kitokovsky ..................... 24/194 |
| 4,896,668 | 1/1990 | Popoff et al. .................... 606/74 |
| 4,920,959 | 5/1990 | Witzel et al. .................... 606/53 |
| 4,943,292 | 7/1990 | Foux ................................ 606/70 |
| 4,944,753 | 7/1990 | Burgess et al. ................. 623/16 |
| 4,955,913 | 9/1990 | Robinson ....................... 606/228 |
| 4,966,600 | 10/1990 | Songer et al. ................... 606/74 |
| 5,024,618 | 6/1991 | Tepic .............................. 606/53 |
| 5,089,012 | 2/1992 | Prou ............................... 606/224 |
| 5,139,498 | 8/1992 | Astudillo Ley ................. 606/69 |
| 5,163,598 | 11/1992 | Peters et al. ................... 227/176 |

FOREIGN PATENT DOCUMENTS

| | | |
|---|---|---|
| 2730571 | 1/1978 | Fed. Rep. of Germany ........ 606/74 |
| 3042699 | 5/1981 | Fed. Rep. of Germany ........ 606/71 |
| 3244680 | 6/1984 | Fed. Rep. of Germany ........ 606/74 |
| 424577 | 5/1911 | France ............................. 24/191 |
| 9210460 | 8/1992 | France . |
| 838178 | 6/1960 | United Kingdom ............... 24/193 |

OTHER PUBLICATIONS

Sirivella, et al., "Improved Technique for Closure of Medium Sternotomy Incision/Mersilene [Ethicon, Inc.] Tapes Versus Standard Wire Closure" *J. Thorac. Cardiovasc. Surg.*, 1987;94:591-5.

(List continued on next page.)

*Primary Examiner*—Tamara L. Graysay

[57] ABSTRACT

A strap assembly to be looped about split portions of human tissue to retain the split portions in adjacent contacting relation to promote healing thereof is provided. The strap assembly includes a flexible strap member and a buckle member to secure the strap member. The buckle member includes a base member having an opening extending therethrough for reception of the strap member and a clip member pivotally mounted to the base member for engaging the strap member. The clip member is adapted to pivot from an open position to allow for reception of the strap member through the opening and a closed position wherein the strap is engaged by and wedged between a forward edge of the clip member and the base member to secure the strap member around the split portions of tissue.

28 Claims, 5 Drawing Sheets

OTHER PUBLICATIONS

Product brochure for Deknatel Inc. (Pfizer) Dekna--Band sternotomy closure system.

Miller et al., "Repair of Sternal Dehiscence Using a Harrington Compression System", *Ann. Thorac. Surg.*, 45:684–685, Jun. 1988.

Product Brochure for Pilling (Fort Washington, Pa. Sternal Approximator and Fixation System).

Mulch et al., "Closure of Longitudinal Sternotomy with Absorbable Sutures", *Thorac. Cardiovasc. Surgeon*, 34, 191–193 (1986).

Johnston, Jr. et al., Mersilene [Ethicon, Inc.] "Ribbon Closure of the Median Sternotomy: An Improvement Over Wire Closure" (1984).

Labitzke et al., "'Sleeve-Rope Closure' of the Median Sternotomy After Open Heart Operatons", *Thorac. Cardiovasc. Surgeon*, 31, 127–128 (1983), pp. 127–128.

Kalush et al., "Peristernal Closure of Median Sternotomy Using Stainless Steel Bands" (1975), pp. 172–173.

Timmes et al., "A New Method of Sternal Approximation", *Ann. Thorac. Surg.*, vol. 16, No. 5, May, 1973, pp. 544–546 [the Wolvek approximator].

Sanfelippo et al., "Nylon Bands for Closure of Median Sternotomy Incisions/An Unacceptable Method", *Ann. Thorac. Surg.*, vol. 13, No. 4, Apr., 1972, pp. 404–406.

LeVeen et al., "Nylon-Band Chest Closure", *Arch. Surg.*, vol. 96, Jan. 1968, pp. 36–39.

Vincent, "Update on Sternal Osteosynthesis", *Ann. Thorac. Surg.*, vol. 41, Feb. 1986, pp. 216–218.

Allied Signal Inc.'s Product brochure for SPECTRA extended chain polyethylene fibers.

Vincent, "Controlled Tension Osteosynthesis A Way To Prevent Or Cure The Cardiac Sternotomy Compliactors".

STERNUM CLOSURE BUCKLE

BACKGROUND OF THE INVENTION

1. Field of the Invention

The present invention relates to surgical devices for repair of split portions of tissue. In particular, the invention is directed to a strap assembly for securing a strap about split portions of a sternum to maintain the portions in adjacent contacting relationship during healing.

2. Description of the Prior Art

During surgery that involves a median sternotomy, e.g., open heart surgery, the sternum is split longitudinally to allow access to the organs within the thoracic cavity. Upon completion of the surgery, the sternum is rejoined and closed securely. For proper healing to occur, the split sternum portions must be engaged in face-to-face relationship and compressed together while the sternum heals.

Traditional methods for closing a sternum involve securing steel wires around or through the sternum halves and approximating the sternum by twisting the wires together.

Recently, a certain amount of emphasis has been directed towards the use of band or strap assemblies for sternum repair. Such assemblies typically include a locking mechanism which secures a strap in a closed looped configuration about the sternum portions. One example of an assembly of this type is described in U.S. Pat. No. 4,813,416 and includes a banding assembly having a curved surgical needle, an attached thin flat stainless steel band and a buckle mechanism. The sternum halves are brought to abutting closure by looping the band in position around or through the sternum portions and securing the band within the buckle mechanism.

While utilization of steel wires and strap assemblies have been widely accepted for sternum repair, certain shortcomings with these devices are apparent. The use of steel wires presents problems to the surgeon during the operation and to the patient after closure is completed. Steel wires are difficult to maneuver and place around the sternum. The wire edges are often sharp and can easily pierce through undesired areas including tissue surrounding the sternum area or the surgeon's gloves or fingers.

The strap assemblies known heretofore incorporate buckle mechanisms which are relatively structurally complex. For example, the buckle mechanism described in U.S. Pat. No. 4,813,416 includes a saddle part, inturned flanges disposed on opposing sides of the saddle part and a loop segment. The saddle part and inturned flanges define a band slide through course for reception of a portion of the band. A spring leaf extends upwardly from the loop segment through a slot in the saddle part. The tip end of the spring leaf is narrowed to define a spring tooth or projection which projects through an aperture formed in the band to maintain the closed band loop in a locked configuration.

Thus, there is a clear need for a surgical device which is simple in construction and effectively secures the divided sternum portions together for healing. The present invention is directed to a strap assembly having a buckle member of relatively simple construction which securably retains a strap in a closed looped locking configuration around sternum portions to maintain the portions in adjacent engaged relation during healing.

SUMMARY OF THE INVENTION

A strap assembly to be looped about split portions of human tissue to retain the split portions in adjacent contacting relation to promote natural healing thereof comprises a strap member and a buckle member. The buckle member includes a base member having an opening extending therethrough for reception of the strap member and means for engaging the strap member received within the opening to securely wedge the strap member against the base member.

In a preferred embodiment, the buckle member comprises a base member having a transverse opening extending therethrough for reception of the strap member and a clip member pivotally positioned in the base member for engaging the strap member received within the opening. The clip member pivots between an open position to allow for reception of the strap member through the opening and a closed position to wedge the strap member between a forward edge of the clip member and the base member to secure the strap member around the tissue. Preferably, the clip member is attached to the strap member such that tightening of the strap member around the split portions of tissue applies a tensional force to the clip member. This force causes the clip member to pivot to the closed position in which the forward edge of the clip member engages the strap member received within the opening to securely wedge and retain the strap member between the forward edge of the clip member and the base member.

The strap member may include handle means to facilitate maneuvering the strap assembly around the split portions of tissue. The handle means may include a looped section of a first end portion of the strap member. A surgical needle may be attached to a second end portion of the strap member to facilitate maneuvering through body tissue.

A method is also disclosed for repairing split portions of body tissue. The method comprises the steps of providing a strap assembly including a flexible strap member and a buckle member. The buckle member includes a base member having an opening extending therethrough for reception of the strap member and a clip member pivotally positioned in the base member for engaging the strap member received within the opening. The method further comprises the steps of looping the strap member around the split tissue portions to be joined, inserting a first end of the strap member through the opening in the buckle member, tightening the looped strap member about the split tissue portions to bring them into adjacent engaged relation and securing the strap member with the buckle member.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
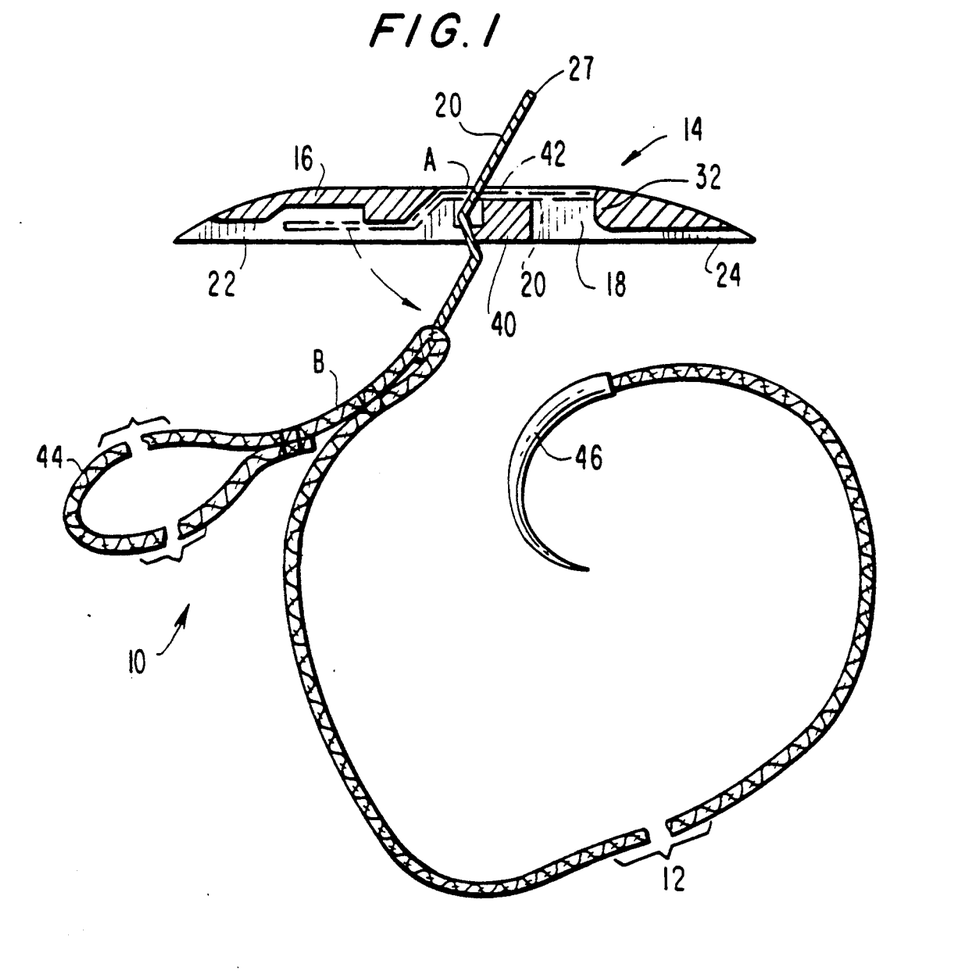
FIG. 1 is a side view in cross-section of the strap assembly constructed according to the present invention, illustrating the buckle member with attached strap member.

Referring initially to FIG. 1, there is illustrated the strap assembly 10 constructed according to the present invention. Strap assembly 10 has particular application in securing split portions of a sternum together after a sternotomy and includes elongated strap 12 and buckle member 14 secured to a first end portion of the strap. Strap 12 may be formed of any material suitable for use in stabilizing fractured bones or securing tissue portions together. Examples of such materials include those fabricated from synthetic fibers such as polyesters, polyethylene, polytetrafluoroethylene and polyamides. In a preferred embodiment, strap 12 is formed from a bioabsorbable material such as catgut or synthetic materials including polymers and copolymers of glycolides, lactides, carbonates and lactones.

U.S. patent application Ser. No. 07/829,423, the contents of which are incorporated herein, discloses a strap or sternum closure ribbon which may be readily adapted for use with the assembly of the present invention. That strap is a braided product having a plurality of elongated filamentary reinforcing members of ultra high molecular weight polyethylene fibers. The fibers may be plasma treated to reduce slip characteristics of the yarn. The fibers exhibit strengths from about 375 kpsi (thousands of pounds per square inch) to 560 kpsi and a tensile module of from about 15 msi (millions of pounds per square inch) to about 30 msi. It is to be appreciated that strap 42 is readily pliable for forming the sternum encircling loop course.

Buckle member 14 includes base member 16 having opening 18 extending through the base member for reception of a portion of a strap and clip member 20 pivotally mounted to base member 16 at position A. Clip member 20 is adapted to pivot between an open position to allow for the passage of the strap within opening 18 and a closed position (shown in phantom) to secure the strap within the buckle. Base member 16 also includes longitudinal grooves 22,24 disposed on the lower surface of base member 16. Grooves 22,24 are configured to accommodate portions of the strap beneath base member 16 when the strap is secured around the split portions of the sternum. This enables the buckle member 14 to rest flatly on the surface of the sternum when in the secured position.

Figure 2:
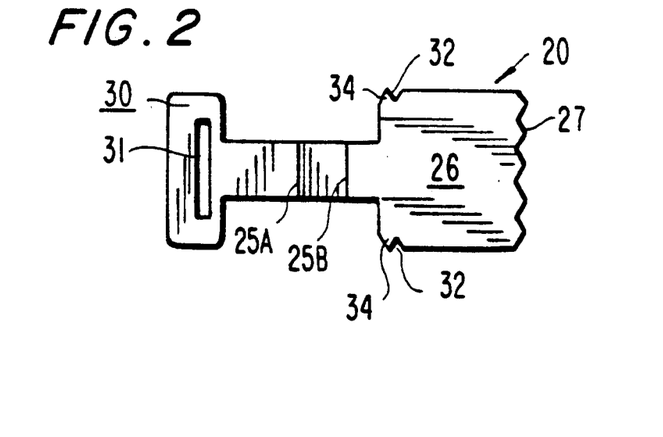
FIG. 2 is a top plan view of the clip member of the buckle member of FIG. 1.
Figure 6:
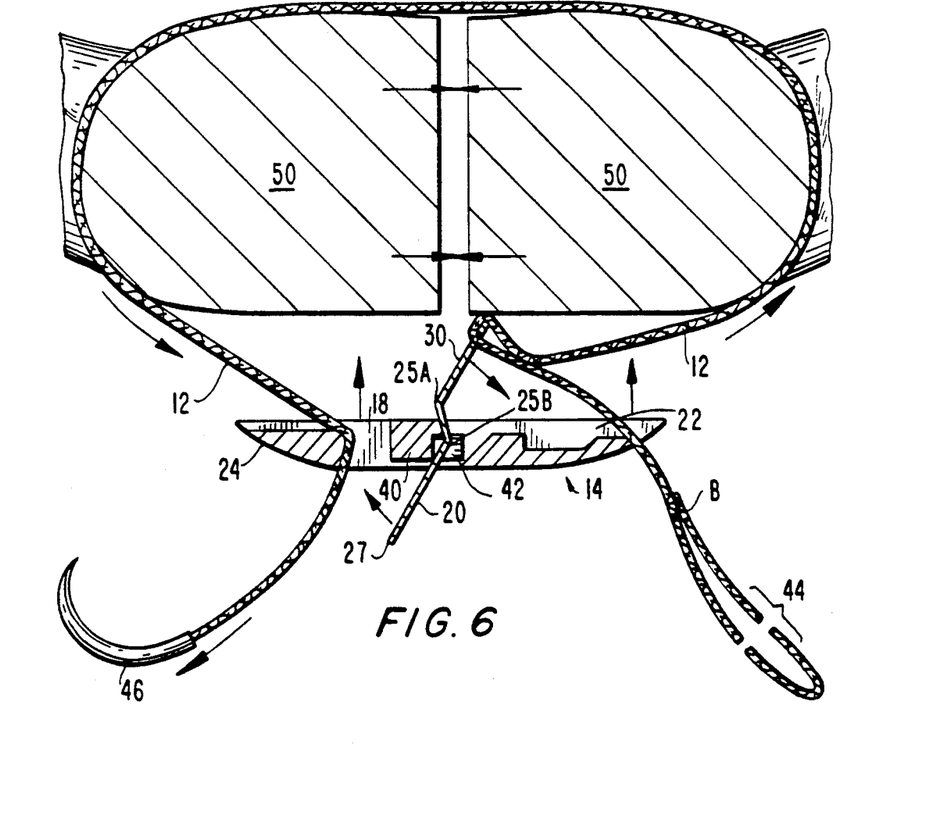
FIG. 6 is an enlarged cross-sectional view taken along lines 6—6 of FIG. 5 illustrating the strap assembly of FIG. 1 in the open position.

Referring now to FIG. 2, clip member 20 is shown and includes head portion 26, intermediate portion 28 and tail portion 30. Head portion 26 includes forward edge 27 which engages strap 12 when buckle 14 is in the locked position. Preferably edge 27 is serrated. Head portion 26 and tail portion 30 are latitudinally displaced relative to each other by bend lines 25A, 25B to provide a generally stepped configuration of clip member 20 (FIGS. 1 and 6). Such stepped configuration enables the clip member to be accommodated by base member 16 when the clip member is in a strap engaging position. Tail portion 30 includes slot 31 which is configured to receive a portion of strap 12 to secure the strap to clip member 20. A pair of opposed notches 32 are formed in head portion 26. Notches 32 define opposed arcuate tabs 34. The notches and tabs are provided to mount clip member 20 to base member 16 as will be described hereinbelow.

Figure 3:
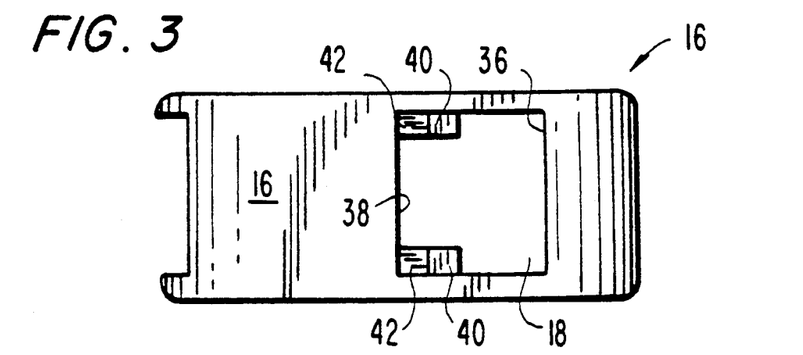
FIG. 3 is a top plan view of the base member of the buckle member of FIG. 1.

Referring now to FIG. 3, base member 16 is illustrated with clip member 20 removed. Opening 18 of base member 16 defines forward edge or ramp 36 and rear edge 38. Typically, ramp 36 may be perpendicular to the longitudinal axis of the base member or at a slight angle, e.g., less than 20° away from the perpendicular, preferably between 12° and 18° away from the perpendicular. Two projections 40 are provided and extend inwardly into opening 18 adjacent rear edge 38. Projections 40 act as a pivot point and assist in stabilizing clip member 20 when the clip member is mounted to the buckle. A depressed groove 42 is formed in each projection 40 adjacent rear edge 38. Grooves 42 are adapted to accommodate arcuate tabs 34 of clip member 20 when the clip member is mounted to the base member.

Figure 4:
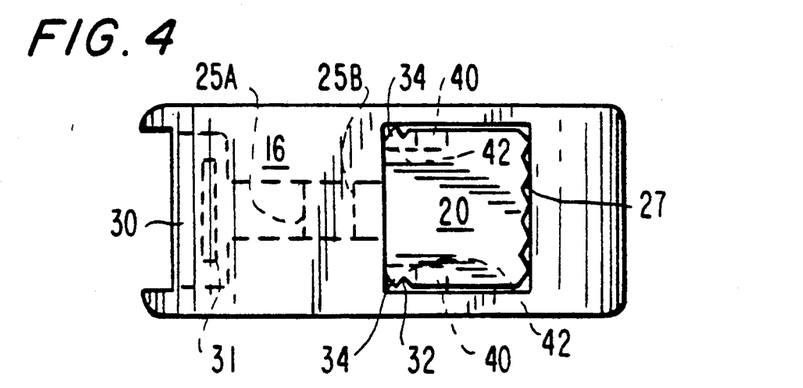
FIG. 4 is a top plan view of the buckle member of FIG. 1, illustrating the clip member mounted to the base member.

FIG. 4 shows clip member 20 mounted within base member 16. Clip member 20 is pivotally mounted to the base member by inserting the clip member within opening 18 and positioning arcuate tabs 34 of the clip member within depressed grooves 42. Thereafter, the upper surface portion adjacent grooves 42 may be deformed by, for example, a peening operation which flattens and displaces base material over arcuate tabs 34 of clip member 20. This displacement may be controlled to enclose tabs 34 within grooves 42 to thereby mount clip member 20 to the base member.

In the alternative, clip member 20 may be mounted to base member 16 by providing a pair of opposing recesses in the base member adjacent grooves 42 to receive corresponding arcuate tabs 34 of the clip member such that tabs 34 snap into the recesses to mount the clip member to the base member. One skilled in the art may readily determine other alternative methods to mount clip member 20 to base member 16.

The components of buckle member 14 are preferably fabricated from a bio-compatible metal such as stainless steel or titanium. Buckle member 14 may also be fabricated from polymeric materials including acrylics, polystyrenes, polycarbonates and styrene-acrylonitrile (SAN) copolymers. It is also possible to fabricate buckle member 14 from a synthetic absorbable material. Such materials are well known in the art and include polymers or copolymers of glycolides, lactides, carbonates, lactones or blends thereof.

Referring again to FIG. 1, strap 12 is attached to tail portion 30 of clip member 20 by passing an end of strap 12 through slot 31 (FIG. 2), and thereafter securing the strap portions adjacent the tail portion by conventional means such as fabric welding, cementing or stitching. Securing strap 12 to clip member 20 as opposed to base member 16 is a significant feature of the present invention in that it provides the mechanism for retaining the strap around sternum halves 50. In particular, as the strap is tightened around the sternum, the formed strap loop applies a tensional force to clip member 20. This force drives clip member 20 to a general horizontal position and against the strap portion received within opening 18 of the buckle member. It is to be appreciated that as the strap loop is tightened around the sternum halves, the tensional forces on the clip member increases. Consequently, as the force increases, the forward edge 27 of clip member 20 is driven even more strongly into the strap portion in a manner to maintain a locking relationship between the buckle and the strap.

A handle 44 may be provided to facilitate maneuvering and tightening of strap 12 around the sternum halves. Preferably, handle 44 is formed by looping a second end portion of strap 12 over itself and then securing the end portion at position B along the strap. Handle 44 enables the user to control and maneuver the strap member from a position relatively remote from the operative site.

A surgical needle 46 may be attached to a first end of strap 12 to assist in penetrating the targeted parasternal location and positioning the strap under the sternum and then outwardly at an opposite parasternal location. A curved surgical needle is appropriate for sternum closure and may be securely attached to the elongated strap by conventional methods. The end portion of strap 12, which is to be attached to needle 46, may be tapered to facilitate the needle-attachment process.

Further understanding of the strap assembly of the present invention will be realized from the description provided of the use of same to secure split portions of a sternum together after surgery.

Figure 5:
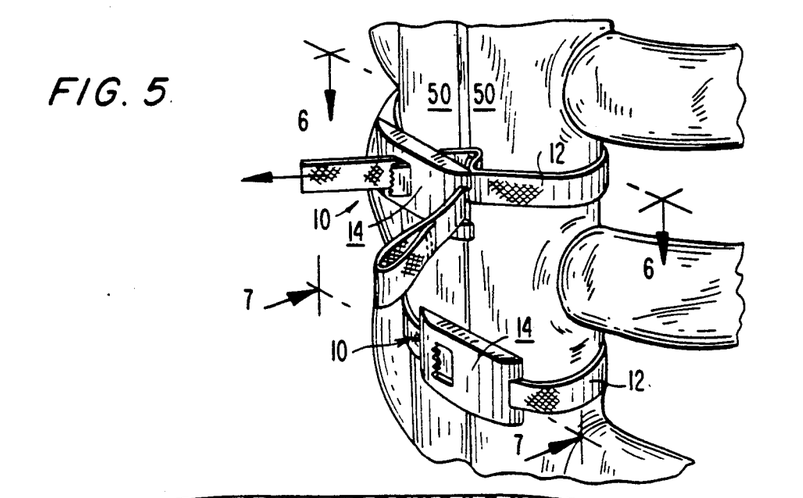
FIG. 5 is a perspective view of the strap assembly of FIG. 1 in a closed looped configuration around sternum portions.

FIG. 5 illustrates two strap assemblies positioned about split sternum portions 50. A first strap assembly 10 is shown positioned around a lower section of sternum portions 50 with buckle member 14 in the fully secured position. A second strap assembly is positioned about an upper section of sternum portion 50, with the buckle member 14 in the unsecured position.

The application of strap assembly 10 around sternum halves 50 to effect sternum closure is accomplished by placing strap 12 including buckle member 14 adjacent a selected parasternal location at one side of the sternum. Needle 46 with attached strap 12 is then inserted within the body tissue and passed under both sternum halves 50 to an opposite parasternal location where it is exposed from the operative site. The needle with attached strap is then pulled from the sternum location until a sufficient working length of strap is provided. Buckle member 14 is grasped with an appropriate surgical implement, such as, for example, a pair of conventional forceps, and clip member 20 is pivoted to a general vertical position to expose opening 18 as shown in FIG. 6. The strap end with attached needle 46 is inserted within opening 18. The needle may be removed from the strap prior to this step if desired. Once through the opening, the surgeon grasps the strap end while holding handle 44 and pulls the strap end in an outward direction to remove most of the slack formed in the loop.

Figure 7:
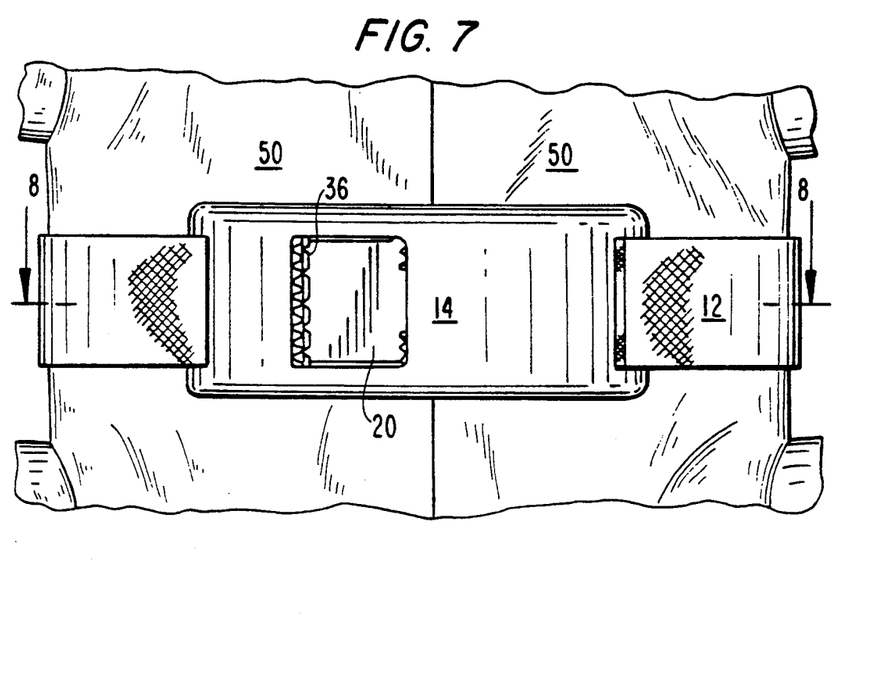
FIG. 7 is an enlarged frontal view taken along the lines 7—7 of FIG. 5 illustrating the strap assembly in the closed position.
Figure 8:
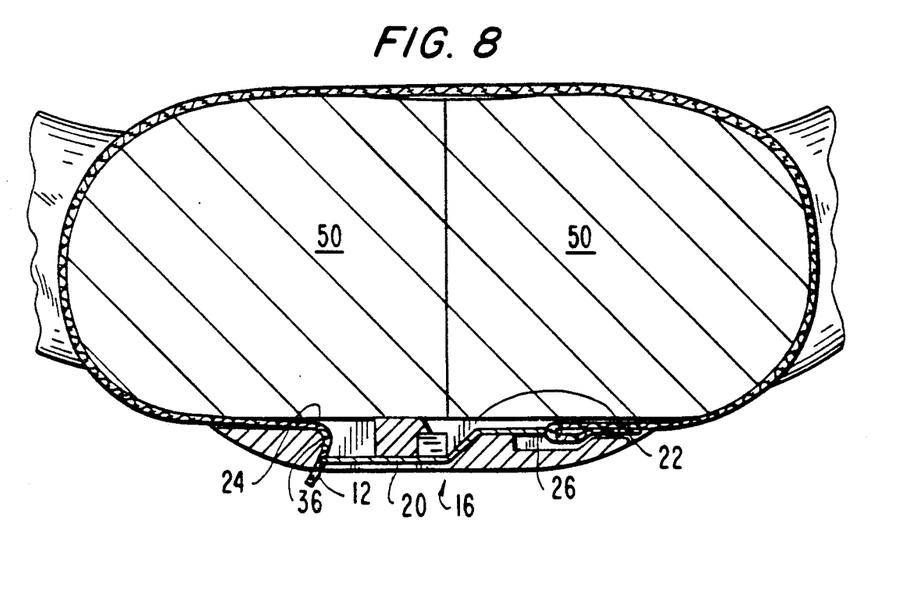
FIG. 8 is an enlarged cross-sectional view taken along lines 8—8 of FIG. 7 illustrating the strap assembly in the secured position.

At this point in the procedure, the strap member is not securely tightened around sternum halves 50. One or more strap assemblies may be placed around selected parasternal locations of the sternum in the same manner. When several strap assemblies are in place around the sternum, each member is ready to be tightened. The surgeon proceeds in grasping handle 44 and removes the remaining slack formed in the loop by pulling on the strap end. The sternum halves are joined together in an adjacent face-to-face relationship and each strap member is tightened around the sternum. FIGS. 7 and 8 illustrate strap 12 in a closed looped locked configuration. In the closed position, forward edge 27 of clip member 20 wedges a portion of strap 12 against ramp 36 of buckle member 14. As previously noted, the formed loop applies a tensional force on clip member 20. This force drives forward edge 27 of clip member 20 into strap 12 to maintain the formed loop in a locking relationship with buckle member 14. The remaining strap assemblies are secured around the sternum in the same manner. Once the buckle assemblies are secured in place, handle 44 and the excess working length of the strap end may be removed.

Figure 9:
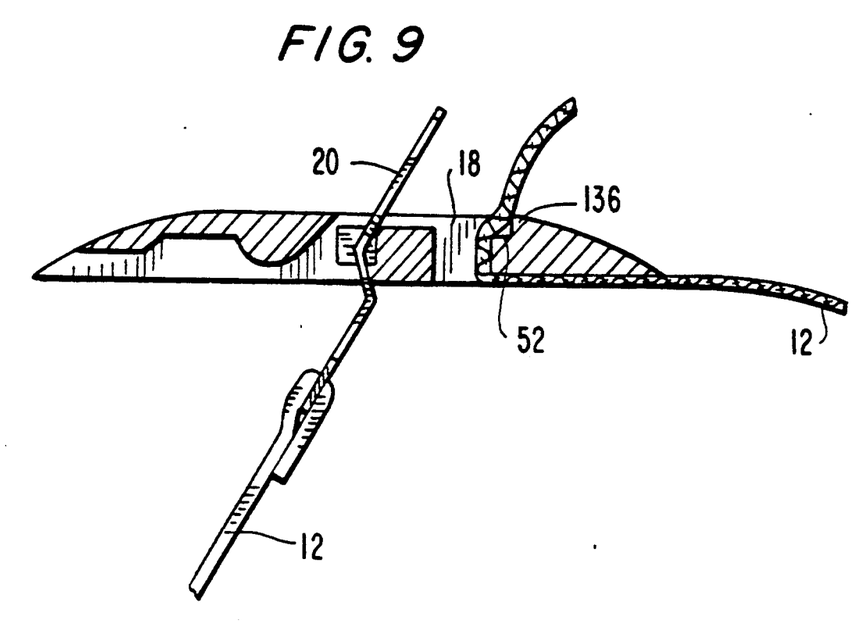
FIG. 9 is a side view in cross-section of an alternative embodiment of the buckle member of the present invention.
Figure 10:
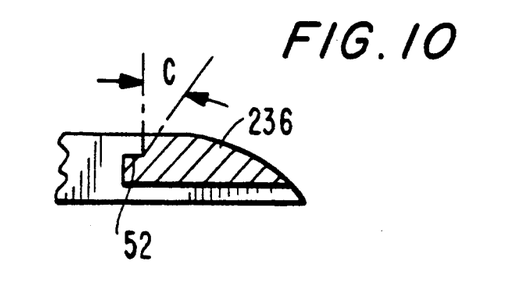
FIG. 10 is a side view of a portion of the embodiment of FIG. 9, modified to show a slanted ramp.

Referring now to FIG. 9, an alternative embodiment of the buckle member of the present invention is illustrated. This embodiment is substantially similar to the embodiment discussed above except for the inclusion of a shelf 52 projecting from ramp 136 and into opening 18. FIG. 9 shows ramp 136 as perpendicular to the longitudinal axis of the buckle. However, the ramp may be slanted away from the opening of the buckle by an angle C of 1° to 20° shown in FIG. 10. Preferably, C ranges from 12° to 18°.

Shelf 52 extends across the width of opening 18 and assists in securing strap 12 to base member 16. In particular, shelf 52 alters the angle in which the strap is received within opening 18 from a position substantially normal to the longitudinal axis defined by base member 16 to a position substantially parallel to the axis, and, as such, impedes sliding movement of the strap through the opening. Shelf 52 also provides more surface area for clip member 20 to engage the strap. Shelf 52 is also configured to receive forward edge 27 of clip member 20 when the clip is in the strap engaging position. The strap member is secured around the sternum halves in substantially the same manner as described in the prior embodiment.

The present invention provides a relatively simple and less traumatic means to effect sternum closure which can be performed rapidly and effectively by the surgeon. While the above description contains many specifics, these specifics should not be construed as limitations on the scope of the invention, but merely as exemplification of preferred embodiments thereof. Those skilled in the art will envision many other possible variations that are within the scope and spirit of the invention as defined by the claims appended hereto.

What is claimed is:

1. A strap assembly to be looped about split portions of a human sternum to retain the sternum portions in adjacent contacting relation to promote healing thereof, comprising:
    a flexible biocompatible strap member and dimensioned to be passed through intercostal tissue and about the sternum portions; and
    a buckle member dimensioned to be positioned adjacent the sternum and having a reduced profile when in a secured position, said buckle member comprising:
    a base member having a lower surface and an upper surface, said base member defining a longitudinal axis and having a transverse opening extending generally transverse to said longitudinal axis for reception of said strap member such that said strap member is passed through said lower surface of said base member and through said transverse opening to extend beyond said upper surface of said base member; and means for engaging said strap member received within said transverse opening to secure said strap member around the sternum portions, said engaging means having a first end portion for wedging said strap member against at least a transverse bearing surface of said base member and a second end portion attached to said strap member, said at least a transverse bearing surface disposed adjacent said transverse opening.

2. The strap assembly according to claim 1, wherein said engaging means comprises a clip member pivotally mounted to said base member, said clip member having a forward edge and a tail end, said clip member attached to said strap member at said tail end thereof and adapted to pivot to a closed position such that said forward edge thereof securely wedges said strap member against a transverse ramp portion of said base member.

3. The strap assembly according to claim 2, wherein said buckle member is fabricated from a material selected from the group consisting of stainless steel and titanium.

4. The strap assembly according to claim 2, wherein said buckle member is fabricated from a polymeric material selected from the group consisting of acrylics, polystyrenes, polycarbonates and styrene-acrylonitrile (SAN) copolymers.

5. The strap assembly according to claim 2, wherein said transverse bearing surface of said base member includes a shelf portion projecting from said ramp portion into said transverse opening, said shelf portion defining a generally planar bearing surface such that in the closed position of said clip member said forward edge of said clip member wedges said strap member against said transverse ramp portion and against said bearing surface of said shelf portion.

6. The strap assembly according to claim 2, further comprising means for attaching said strap member to said tail end of said clip member.

7. The strap assembly according to claim 6, wherein said attaching means includes a slotted opening formed in second end said tail end of said clip member, said slotted opening configured and adapted for reception of said strap member.

8. The strap assembly according to claim 2, wherein said forward edge of said clip member is serrated.

9. The strap assembly according to claim 2, wherein two longitudinal grooves are disposed on said lower surface of said base member, said grooves being configured and dimensioned to accommodate portions of said strap member beneath said base member when said strap member is secured around the split portions of tissue.

10. The strap assembly according to claim 2, further comprising handle means associated with said strap member to facilitate maneuvering of said strap member around the split portions of tissue.

11. The strap assembly according to claim 10, wherein said handle means comprises a looped section of a second end portion of said strap member.

12. The strap assembly according to claim 2, further comprising a surgical needle attached to a first end portion of said strap member.

13. The strap assembly according to claim 1, wherein said strap member is formed at least in part of ultra-high molecular-weight polyethylene fibers.

14. The strap assembly according to claim 1, wherein said strap member comprises synthetic fibers selected from the group consisting of polyesters, polyethylene, polytetrafluoroethylene and polyamides.

15. The strap assembly according to claim 1, wherein said strap member comprises a bioabsorbable material selected from the group consisting of catgut and synthetic materials including polymers and copolymers of glycolides, lactides, carbonates and lactones.

16. A strap assembly to be looped about split portions of tissue to retain the split portions in adjacent contacting relation to promote healing thereof, comprising:

a flexible strap member adapted to be looped about split portions of tissue; and a buckle member comprising:

a base member defining a longitudinal axis and having a transverse opening for reception of said strap member, said base member further including a transverse ramp portion and a shelf portion projecting from said transverse ramp portion into said transverse opening;

a clip member pivotally mounted within said transverse opening to said base member and adapted for pivotal movement between an open position for reception of said strap member through said transverse opening and a closed position to secure said strap member within said buckle member; and wherein said clip member is attached to said strap member such that tightening of said strap member about the split portions of tissue exerts a longitudinal closing force on said clip member to cause said clip member to pivot to the closed position whereby said clip member, said transverse ramp portion and said shelf portion cooperatively secure said strap member within said buckle member.

17. The strap assembly according to claim 16, wherein said ramp portion defines a ramp surface generally transverse to a longitudinal axis defined by said base member.

18. The strap assembly according to claim 16, wherein said ramp portion defines a ramp surface which is angularly displaced relative to a plane generally transverse to a longitudinal axis defined by said base member.

19. The strap assembly according to claim 18, wherein said ramp surface is displaced relative to said transverse plane by an angle ranging from about 1° to about 20°.

20. The strap assembly according to claim 19, wherein said ramp surface is displaced relative to said transverse plane by an angle ranging from about 12° to about 18°.

21. A method for repairing split portions of tissue, comprising the steps of:

providing a strap assembly including a strap member and a buckle member, said buckle member including a base member having a transverse opening for reception of said strap member and a clip member pivotally mounted to said base member and adapted for pivotal movement from an open position to permit passage of said strap member through said opening and a closed position to wedge said strap member between a forward edge of said clip member and said base member to secure said strap member around the split portions of tissue;

looping said strap member around the tissue portions;

inserting a first end of said strap member through said opening in said buckle;

advancing said first end of said strap member in a tensioning direction to tighten the looped strap member to a predetermined tension about the split portions of tissue so as to position the tissue portions in an adjacent engaged relation; and releasing said first end portion of said strap member such that the tensional forces applied to said strap member during tensioning thereof causes said clip member to pivot to the closed position such that said forward edge of said clip member wedges said strap member against said base member.

22. A method for securing first and second portions of a sternum to retain the portions in adjacent engaged relation during healing, comprising the steps of:

providing a strap assembly including a flexible strap member and a buckle member, said buckle member including a base member having an opening extending therethrough for reception of said strap member and a clip member pivotally mounted to said base member and adapted for pivotal movement from an open position to allow for reception of said strap member through said opening and a closed position to wedge said strap member between a forward edge of said clip member and said base member to secure said strap member around the split portions of tissue;

inserting a first end of said strap member through intercostal tissue along an outer edge of the first sternum portion;

maneuvering said first end under the first and second sternum portions to expose the first end along an outer edge of the second sternum portion;

inserting said first end of said strap member through said opening in said buckle member to form a loop about said first and second portions of sternum;

advancing said first end of said strap member in a tensioning direction to tighten said looped strap member about the sternum portions in a manner to position the portions in adjacent engaged relation; and releasing said first end portion of said strap member upon achieving a predetermined tension in said strap member such that the tensional forces applied to said strap member during tensioning thereof causes said clip member to pivot to the closed position whereby said forward edge of said clip member securely wedges said strap member against said base member.

23. A strap member to be looped about split portions of tissue to retain the split portions in adjacent contacting relation to promote healing thereof, which comprises:

a strap member adapted to be looped about split tissue portions; and a buckle member attached to said strap member for securing said strap member in a looped tensioned condition about the split tissue portions, said buckle member comprising:

a base member defining a longitudinal axis, said base member including a transverse opening extending therethrough for reception of said strap member and two longitudinal grooves disposed on a lower surface portion thereof, said longitudinal grooves dimensioned to accommodate portions of said strap member disposed beneath said base member when said strap member is secured around the split tissue portions; and means for engaging said strap member received within said transverse opening to secure said strap member in the looped tensioned condition.

24. The strap assembly according to claim 23 wherein said strap assembly is dimensioned to be secured about split portions of human sternum.

25. A strap member to be looped about split portions of tissue to retain the split portions in adjacent contacting relation to promote healing thereof, comprising:

a strap member adapted to be looped about split portions of tissue;

a buckle member attached to said strap member, comprising:

a base member defining a longitudinal axis, said base member including a transverse opening extending therethrough for reception of said strap member and at least one longitudinal groove formed on a lower surface portion thereof, said at least one longitudinal groove dimensioned to accommodate portions of said strap member passing beneath said base member when said strap member is secured about the tissue portions; and a clip member pivotally mounted within said opening to said base member and adapted to pivot between an open position to permit passage of said strap member through said opening of said base member and a closed position to securely wedge said strap member against said base member.

26. The strap assembly according to claim 25 wherein said base member includes two said longitudinal grooves, a first of said grooves formed in a first end portion of said base member and a second of said grooves formed in a second end portion of said base member.

27. A strap member to be looped about split portions of tissue to retain the split tissue portions in adjacent contacting relation to promote healing thereof, which comprises:

a flexible strap member adapted to be looped about split portions of tissue;

a buckle member comprising a base member defining a longitudinal axis and having a transverse opening for reception of said strap member and a clip member attached to said strap member, said clip member pivotally mounted within said opening of said base member and adapted to pivot between an open and a closed position, said base member including a transverse ramp portion and a shelf portion projecting from said transverse ramp portion into said opening, said shelf portion defining a substantially planar surface such that when said clip member is pivoted to said closed position a forward engaging edge of said clip member wedges said strap member against said planar surface of said shelf portion and against said transverse ramp portion of said base member.

28. The strap assembly according to claim 27 wherein said strap assembly is dimensioned to be secured about split portions of a human sternum.

* * * * *